(12) United States Patent
Shibata

(10) Patent No.: US 6,755,526 B2
(45) Date of Patent: *Jun. 29, 2004

(54) FUNDUS CAMERA

(75) Inventor: Naohisa Shibata, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/151,996

(22) Filed: May 22, 2002

(65) Prior Publication Data

US 2002/0176050 A1 Nov. 28, 2002

(30) Foreign Application Priority Data

May 25, 2001 (JP) ........................................ 2001-156821

(51) Int. Cl.[7] ................................................. A61B 3/14
(52) U.S. Cl. ...................................................... 351/206
(58) Field of Search ................................. 351/205, 206, 351/211, 221

(56) References Cited

U.S. PATENT DOCUMENTS

| | | |
|---|---|---|
| 4,068,932 A | 1/1978 | Ohta et al. |
| 4,279,478 A * | 7/1981 | Matsumura ................. 351/206 |

FOREIGN PATENT DOCUMENTS

| | | |
|---|---|---|
| EP | 1 183 992 A2 | 3/2002 |
| JP | B2 60-57855 | 12/1985 |
| JP | B2 63-22823 | 5/1988 |
| JP | A 8-308802 | 11/1996 |
| JP | A 9-173298 | 7/1997 |
| JP | A 11-169349 | 6/1999 |

* cited by examiner

Primary Examiner—George Manuel
(74) Attorney, Agent, or Firm—Oliff & Berridge, PLC

(57) ABSTRACT

The present invention intends to provide a fundus camera which enables an examiner to easily place a position for presenting the fixation target at an intended position. The fundus camera comprises an observation optical system having an objective lens and a photographic element for photographing a fundus of an eye to be examined via the objective lens, the fundus being illuminated by illumination light for observation, a monitor on which an image of the photographed fundus is displayed, a fixation-target presenting optical system for presenting a fixation target via the objective lens so that the fixation target is visually identified by the eye, a fixation-target moving unit by which a position for presenting the fixation target is moved to a desired position, a first display control unit by which the position of the fixation target to be moved is superposed on the fundus image to be displayed on the monitor, and a second display control unit by which a guide index for moving the fixation target is displayed at a desired position on the monitor.

10 Claims, 6 Drawing Sheets ns in a fundus camera of non-midriasis type consistent with an embodiment of the present invention;

FUNDUS CAMERA

BACKGROUND OF THE INVENTION

1. Field of the Invention

The present invention relates to a fundus camera for photographing a fundus of an eye to be examined.

2. Description of Related Art

A fundus camera having a fixation target (fixation light) guiding a line of sight of an examinee (the eye to be examined) has been known, and it is configured such that the fixation target is movable to a desired position for presenting it in order to photograph a peripheral portion of the fundus. Further, as this kind of fundus camera, such has been proposed that a fixation target image is optically or electrically synthesized and displayed with a fundus image on a monitor for observation, whereby the position for presenting the fixation target can be confirmed.

The fundus camera described above has flexibility in placing the fixation target at a position for presenting it. However, in the case where the examiner intends to photograph the fundus at a position (including an angle) where the fixation target has been previously presented, it is difficult for him to bring the fixation target back to that position. Accordingly, there has been a problem that photographing is a time-consuming task.

SUMMARY OF THE INVENTION

The present invention has been made in view of the above circumstances and has an object to overcome the above problems and to provide a fundus camera which enables an examiner to easily place a position for presenting the fixation target at an intended position.

To achieve the objects and in accordance with the purpose of the present invention, as embodied and broadly described herein, a fundus camera comprises an observation optical system having an objective lens and a photographic element for photographing a fundus of an eye to be examined via the objective lens, the fundus being illuminated by illumination light for observation, a monitor on which an image of the photographed fundus is displayed, a fixation-target presenting optical system for presenting a fixation target via the objective lens so that the fixation target is visually identified by the eye, a fixation-target moving unit by which a position for presenting the fixation target is moved to a desired position, a first display control unit by which the position of the fixation target to be moved is superposed on the fundus image to be displayed on the monitor, and a second display control unit by which a guide index for moving the fixation target is displayed at a desired position on the monitor.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
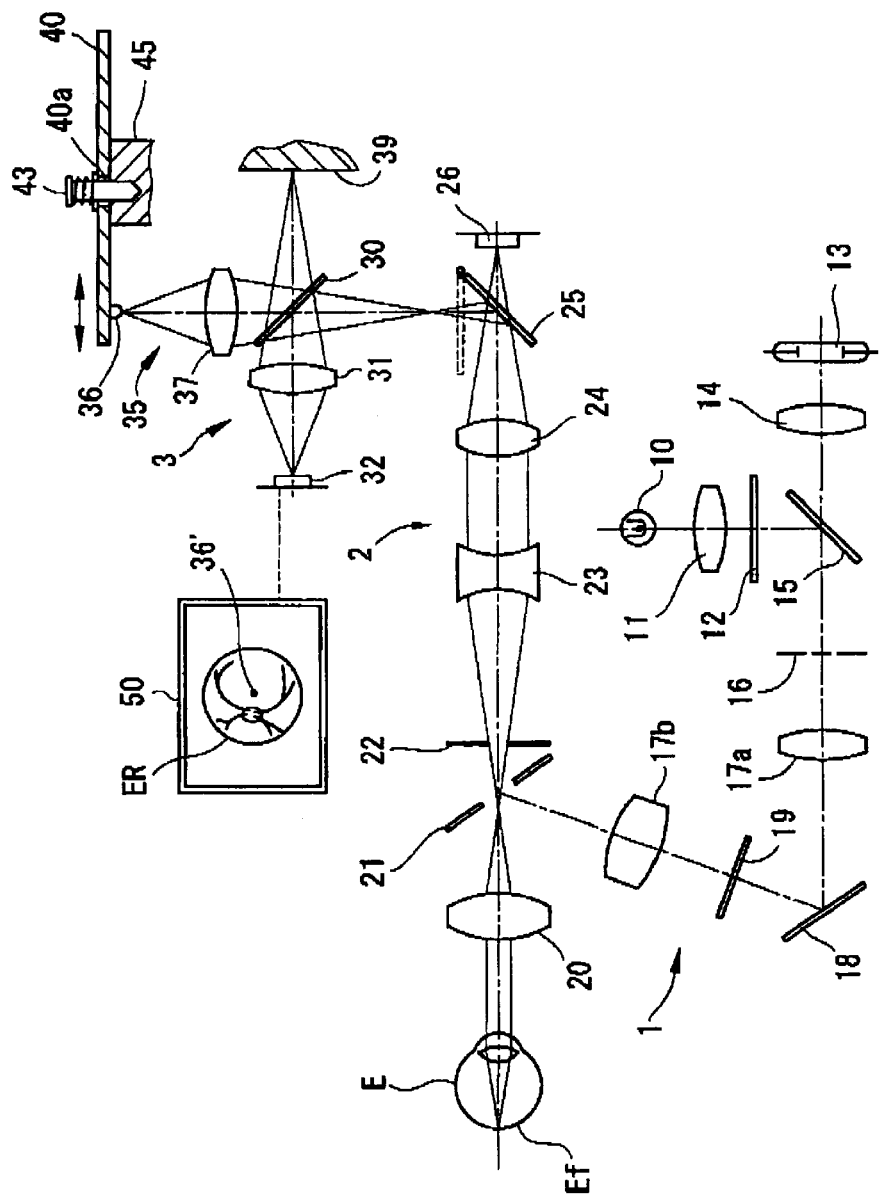
FIG. 1 is a view showing a schematic configuration of an optical system in a fundus camera of non-mydriasis type consistent with an embodiment of the present invention.

A detailed description of a preferred embodiment of a fundus camera consistent with the present invention will now be given referring to the accompanying drawings. FIG. 1 is a view showing a schematic configuration of an optical system in a fundus camera of non-midriasis type. The optical system is provided with an illumination optical system 1, a photographing optical system 2, an observation optical system 3, and a fixation-target presenting optical system 35.

<Illumination Optical System>

Illumination light emitted from a halogen lamp 10 being an illumination light source for observation passes through a condenser lens 11 to be converted into infrared illumination light by an infrared filter 12 having a wavelength-selecting property of transmitting infrared light. Thereafter, the light is reflected by a half mirror 15 and illuminates a ring slit 16 having a ring-shaped aperture. Alternatively, instead of the halogen lamp 10, it may be possible to use such an infrared light source as an infrared LED, which would eliminate the need for the filter 12. Besides, instead of the half mirror 15, it may also be possible to use a dichroic mirror having a wavelength-selecting property of reflecting infrared light and transmitting visible light.

Visible illumination light emitted from a flash lamp 13 being a light source for photographing passes through a condenser lens 14, and is transmitted by the half mirror 15 to be made coaxial with the infrared illumination light, so that the visible illumination light illuminates the ring slit 16.

The illumination light having passed through the slit 16 (ring-slit light) forms an intermediate image in the vicinity of an aperture of an apertured mirror 21 via a relay lens 17a, a mirror 18, a black-dot plate 19 with a small black dot in its center, and a relay lens 17b. The light is then reflected to be coaxial with an optical axis of the photographing optical system 2. Once the illumination light (the ring-slit light) reflected by the mirror 21 forms an image via an objective lens 20 in the vicinity of the pupil of an eye E to be examined, the light is diffused to illuminate a fundus Ef of the eye E uniformly. When entering the lens 20, the illumination light (the ring-slit light) may generate some amount of reflected light which would be detrimental at the time of observing and photographing an image of the fundus Ef. Therefore, it is arranged that the detrimental light should be absorbed by the small black dot provided in the center of the black-dot plate 19.

<Photographing Optical System>

Once the light reflected from the fundus Ef forms an intermediate image of the fundus Ef via the lens 20, the reflected light enters a return mirror 25 through the aperture of the mirror 21, a photographic diaphragm 22, a focusing lens 23 movable in the direction of the optical axis, and an image forming lens 24. The return mirror 25 is placed in a position indicated by solid lines at the time of observation while it is placed in a position indicated by broken lines at the time of photographing. The visible light reflected from the fundus Ef, which is not reflected by the return mirror 25 when the mirror 25 is placed in the position of the broken lines, enters a photographic color CCD camera 26 having a sensitivity to the visible region, and then forms an image of the fundus Ef on an imaging surface of the camera 26.

<Observation Optical System>

The observation optical system 3 shares an optical path from the lens 20 to the return mirror 25 with the photographing optical system 2. The return mirror 25 is placed in the position of the solid lines except when photographing is performed. A half mirror 30 has a reflectance larger than a transmittance it has. On an optical path in the direction of reflection from the half mirror 30 are placed a relay lens 31 and an observation CCD camera 32 having a sensitivity to the visible region through the infrared region. The infrared light reflected from the fundus Ef, which is reflected by the return mirror 25 when the mirror 25 is placed in the position of the solid lines, is further reflected by the half mirror 30, and then enters the camera 32 through the lens 31 to form an image of the fundus Ef on an imaging surface of the camera 32. Output from the camera 32 is routed to a color monitor 50 which doubles as a monochrome monitor, so that a fundus image ER is displayed on the monitor 50.

<Fixation-target Presenting Optical System>

A fixation-target presenting optical system 35 comprises a point light source 36 as a fixation target and a relay lens 37, and shares the optical path from the return mirror 25 to the lens 20 with the observation optical system 3 via the half mirror 30. The point light source 36 is mounted on a lever 40, so that the lever 40 is manipulated to move the point light source 36 within a plane approximately conjugate with the fundus Ef and the imaging surface of the camera 32. The lever 40, in which an oblong hole 40a is formed, is retained on an enclosure part 45 of the fundus camera by a screw 43 and the like, so that the lever 40 can slide smoothly. Part of the lever 40 extends off the enclosure part 45, permitting an examiner to operate the lever 40 to move the point light source 36, so that he can guide a desired part of the fundus Ef (a line of sight of the eye E).

In addition, a reflecting mirror 39 is provided in the opposite side of the lens 31 across the half mirror 30. The mirror 39 is disposed in a position approximately conjugate with the imaging surface of the camera 32 via the lens 31 and also approximately conjugate with the point light source 36 via the lens 37. When the point light source 36 is lit, part of its light is reflected by the half mirror 30 and heads for the mirror 39, whereby the light is reflected again and returns to the mirror 30. Part of the returning light is transmitted by the half mirror 30, and then forms an image on the imaging surface of the camera 32 via the lens 31. Thus, an image 36' of the fixation target is superposed on the fundus image ER to be displayed on the monitor 50 (The position of the fixation target on the fundus image ER is indicated).

Figure 2:
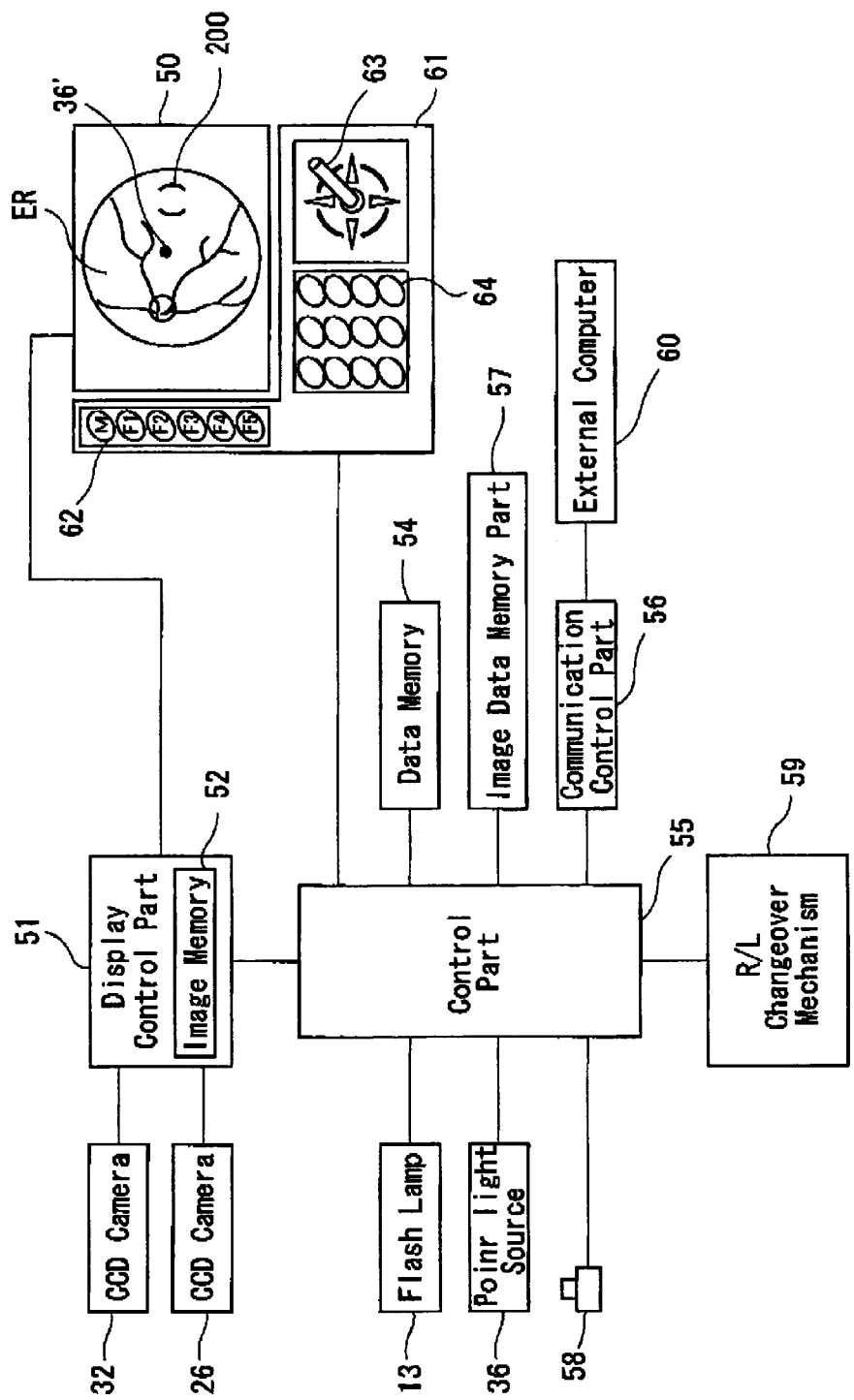
FIG. 2 is a block diagram of primary parts of a control system in the present fundus camera.

FIG. 2 is a block diagram of the primary parts of a control system in the present fundus camera. Outputs from the cameras 32 and 26 are inputted to a display control unit 51 which controls the display on the monitor 50. The display control unit 51 receives a control signal from a control unit 55 which controls the entire fundus camera, and it graphically creates a mark 200 and the like for indicating a position to which the fixation target is to be moved. The mark 200 and the like are synthesized and displayed with the fundus image ER (the observed image) from the camera 32 on the monitor 50. Further, the fundus image (the photographed image) from the camera 26 is temporarily stored in the image memory 52 included in the display control unit 51. Then, the control signal from the control unit 55 shifts the output from the display control unit 51 so that the fundus image from the camera 26 is shown in color on the monitor 50.

The control unit 55 connects to an input unit 61, a nonvolatile data memory 54, an image data memory unit 57, a photographing switch 58, an RIGHT/LEFT changeover mechanism 59 for shifting between the right and left eyes to be examined, and the like. The input unit 61 includes a group of switches 62 individually functioning in accordance with the display on the monitor 50, a ten-key numeric keypad 64, and a lever 63 for inputting the control signal to move the mark 200 and the like on the monitor 50. Also, the control unit 55 can connect to an external computer 60 via a communication control unit 56 which controls data conversion, thereby transferring and outputting the image data stored in the image data memory unit 57. The image data memory unit 57 is a nonvolatile memory such as a PC card which is attachable and removable.

A description will now be given to operations performed in the above-described configuration. First, how to move the fixation target (point light source 36) to a desired position for photographing will be explained. The screen on the monitor 50 is placed in an alignment mode using a mode-changeover switch of the switch group 62 in this case.

An image of the eye E illuminated by infrared light from the lamp 10 and through the filter 12 is formed on the photographing surface of the camera 32, and the formed image is displayed on the monitor 50 via the display control unit 51. An examiner performs alignment (position adjustments) of a main body of the fundus camera with respect to the eye E. Also, he moves the lens 23 to achieve proper focus. When he lights the point light source 36, the light is collected into the fundus Ef through the lens 37, the half mirror 30, the return mirror 25, the lens 24, the lens 23, the diaphragm 22, the aperture of the mirror 21, and the lens 20. Thus, an examinee (the eye E) visually identifies the point light source 36 as a fixation target, and the line of sight of the examinee (the eye E) is guided accordingly.

Part of the light emitted from the point light source 36, which has been reflected by the mirror 30, is further reflected by the mirror 39, and the reflected light forms an image on the photographing surface of the camera 32 via the half mirror 30 and the lens 31. As a result, the fixation-target image 36' is displayed on the monitor 50 as well as the fundus image ER.

While observing the fundus image ER and the fixation-target image 36' on the monitor 50, the examiner operates the lever 40 to move the point light source 36 to a desired position so that he may observe a desired part of the fundus Ef. When he determines a position to be photographed, he depresses the switch 58 to perform photographing.

Figure 3A:
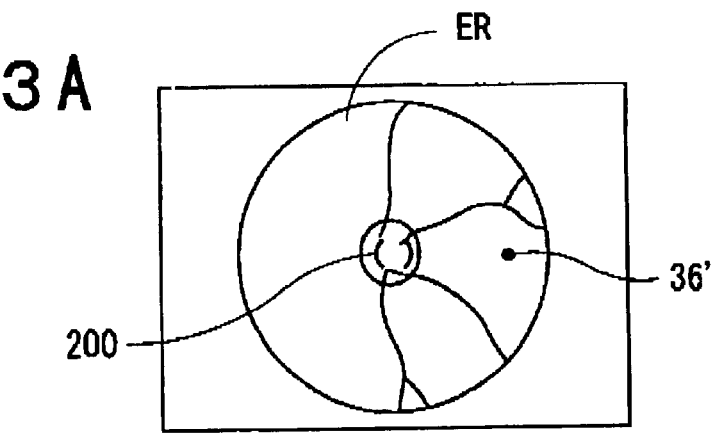
FIGS. 3A, 3B and 3C are views to illustrate setting a position for displaying a guide mark.

Next, a description will be given about forming (displaying) on the monitor 50 a mark for indicating a desired position to which the fixation target (the point light source 36) is to be moved. The examiner presses a mark-setting switch of the switch group 62 to place the screen of the monitor 50 in a mark-setting mode. In this mode, as shown in FIG. 3A, the display control unit 51 creates and graphically displays the guide mark (index) 200 as an intended position to which the fixation-target image 36' is to be moved on the monitor 50 together with a moving picture (the observed image) from the camera 32. In the present embodiment, the guide mark 200 is parentheses in which the fixation-target image 36' is placed, but it may take any shape. For example, when the peripheral portion of the fundus Ef is divided every 60 degrees to be photographed, the guide mark 200 may be line marks radially extending every 60 degrees with reference to a photographing center.

Figure 3B:
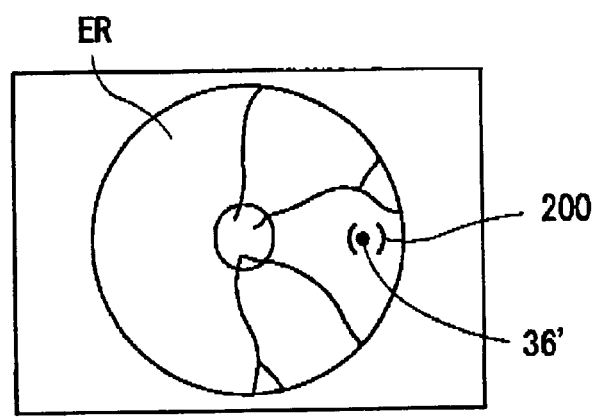

While the examiner observes the fundus image ER and the fixation-target image 36' on the monitor 50, he operates the lever 40 to move the point light source 36 to a desired position, so that he can observe the desired part of the fundus Ef. For example, the examiner may determine a part to be photographed by guiding the line of sight of the examinee (the eye E) to such a position where a papilla is placed at the center of the image. When the examiner determines the position to be photographed, he operates the lever 63 to move the mark 200 to the position of the fixation-target image 36' (see FIG. 3B). Then, after confirming the position of the mark 200, he presses a position-determining switch of the switch group 62. This switch signal allows the data memory 54 to store coordinates of the mark 200 on the monitor 50.

Figure 3C:
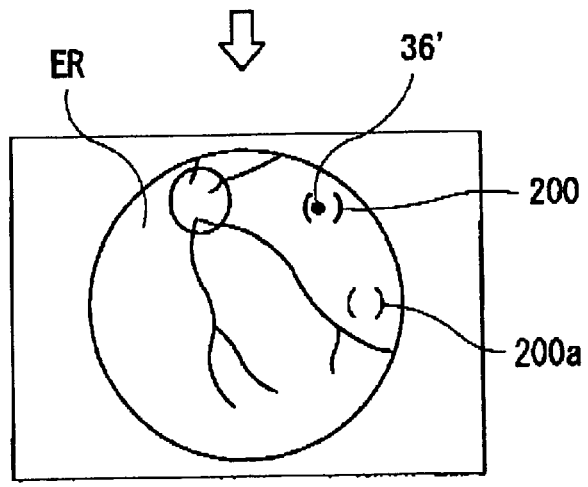

Further, when setting more than one position for displaying the guide mark 200 for the fixation target, the examiner operates the lever 40, as in the above case, in order to move the point light source 36 for guiding the line of sight of the examinee (the eye E). Then, as in FIG. 3C, he operates the lever 63 to move the mark 200 to the position of the fixation-target image 36'. Thereafter, he presses the position-determining switch to store the coordinates in the data memory 54. In FIG. 3C, a mark 200a is shown fixedly at a position having already been set. When a position for displaying the guide mark 200 is further added, the above operations should be repeated.

When more than one position for displaying the guide mark 200 is set while the screen of the monitor 50 remains in the mark-setting mode in this manner, the data memory 54 stores a placement pattern based on the coordinates of each guide mark 200 in one-sheet form. When the mark-setting switch is pressed again, the screen of the monitor 50 returns from the mark-setting mode to the alignment mode in which photographing is allowed.

Figure 4:
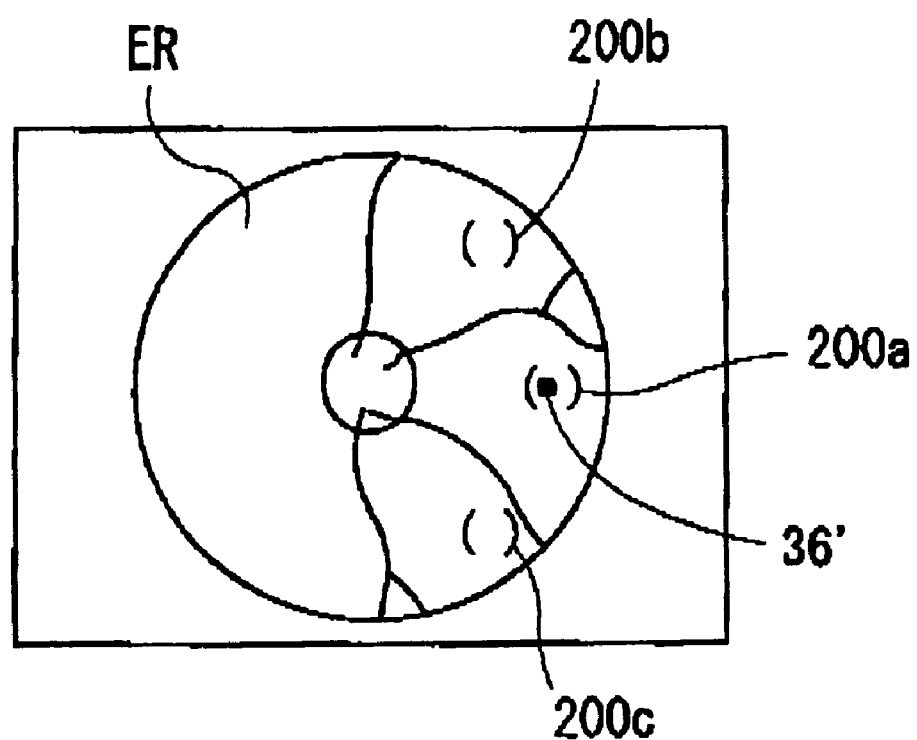
FIG. 4 is a view to illustrate photographing in accordance with the guide mark.

A description will be given about photographing in accordance with the guide mark 200 of which display position is set in the above manner. In the alignment mode, a mode of displaying the guide mark 200 is selected by pressing a switch of the switch group 62. On the monitor 50, the sheet of the placement pattern of the guide mark 200 having been stored in the data memory 54 is retrieved as it is superimposed on the fundus image ER. FIG. 4 is a screen example at this point, and three guide marks 200a, 200b, and 200c are shown on the monitor 50. While the examiner observes the monitor 50, he operates the lever 40 to move the point light source 36, so that the fixation-target image 36' on the monitor 50 is placed at the center of the mark 200a. Then, he presses the photographing switch 58 to perform photographing. Photographing in accordance with the marks 200b and 200c is performed in the same manner as the fixation-target image 36' is placed at the center of each of the marks 200b and 200c.

In this manner, since the examiner can move the fixation target (the point light source 36) in accordance with the guide mark(s) 200 (200a to 200c), he can move the fixation target easily, and reproducibility can be enhanced at the time of photographing the same part of the fundus Ef. Accordingly, for comparing time-varying changes of the same eye to be examined, for example, an accurate photographed image can be obtained. Further, in a group medical examination, photographing at the same position of the fixation target can be performed swiftly.

Incidentally, it is possible to set plural sheets of the placement patterns having different positions for displaying the guide marks 200 and to store them in the data memory 54. In this case, on the screen in the mode of displaying the guide mark(s) 200, one of the sheets of the placement pattern stored in the data memory 54 is selectively retrieved and displayed by pressing a pattern-selecting switch of the switch group 62.

In addition, in the mark-setting mode, the examiner can retrieve any one of the sheets of the placement pattern of the guide mark(s) 200 stored in the data memory 54 to delete any existing guide mark(s) 200 from an unnecessary position or to add a new guide mark 200 to a necessary position.

Figure 5A:
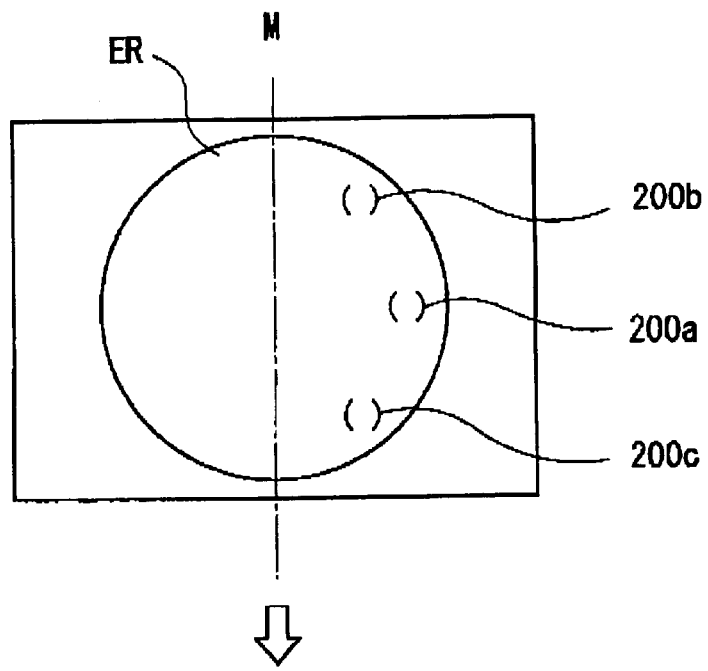
FIGS. 5A and 5B are views to show an example in which the position for displaying the guide mark is flipped from side to side by an R/L changeover mechanism.
Figure 5B:
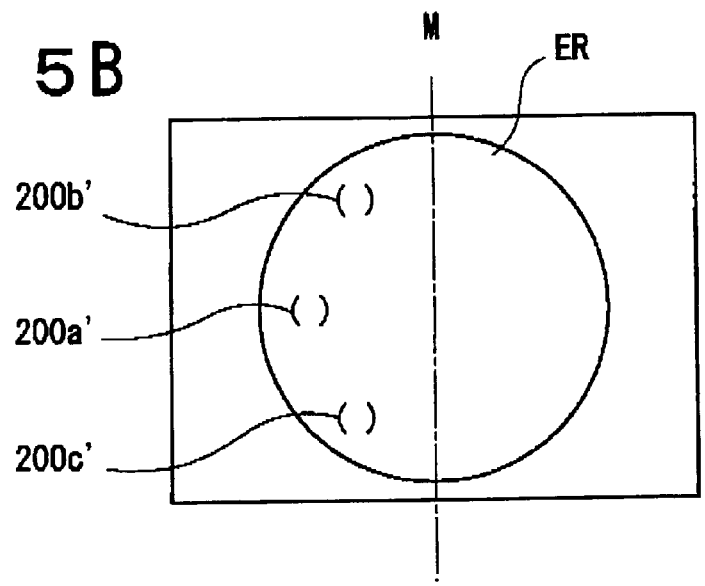

Further, when the sheet of the placement pattern of the guide mark(s) 200 is stored in the data memory 54, it may be preferable that changeover information of the right and left eyes in the mark-setting mode be additionally stored at the same time. FIG. 5A shows an example in which the left eye is designated by the R/L changeover mechanism 59, and the three marks 200a, 200b, and 200c are set as in the case of FIG. 4. At the time of photographing the right eye, the eye E is shifted from the left eye to the right eye by the R/L changeover mechanism 59. When receiving a changeover signal for shifting to the right eye, the control unit 55 outputs a control signal to the display control unit 51. As shown in FIG. 5B, in accordance with the changeover signal (control signal) for shifting between the right and left eyes, the display control unit 51 displays marks 200a', 200b', and 200c' at positions determined by flipping the positions from side to side where the marks 200a, 200b, and 200c are displayed with reference to a vertical axis M running through the center of the fundus image ER shown on the monitor 50. Since the fundus images ER of the right and left eyes are approximately mirror images to each other, the positions set for presenting the guide mark(s) 200 corresponding to one of the eyes provides position data for the other eye, which are obtained by flipping the positions in the data from side to side. This simplifies a procedure of setting the guide mark(s) 200. Furthermore, it is possible to accurately photograph the right and left eyes in a state where the positions for displaying the guide mark(s) 200 for the fixation target on the right side are approximately the same as those on the left side.

As the R/L changeover mechanism 59, not only a changeover mechanism using a switch, but also a conventional mechanism which judges the right and left eyes automatically can be employed. For example, a fundus camera of which main body can be moved in a side-to-side direction (a direction of an eye width) on a base where a chin rest is fixed may include a means for electrically or optically detecting a position of the main body of the fundus camera moving side to side with respect to a center of the base. The detection signal can judge whether the eye E to be examined is the right or left eye.

In the above description, the position on the monitor 50 where the guide mark 200 is formed (displayed) is stored in the data memory 54 as the coordinates on the monitor 50, but it may be stored as the position for presenting the fixation target (the point light source 36). For example, a mechanism for detecting the position of the point light source 36 with respect to a photographing optical axis (a conventional mechanism such as a potentiometer can be used) can directly indicate the position of the point light source 36, thereby determining the position for forming (displaying) the guide mark 200 on the monitor 50 based on the detected position. In the mark-setting mode, when the lever 40 is operated to move the point light source 36, and when the position-determining switch is pressed, the detected position to which the fixation target has been moved is stored in the data memory 54. This allows the guide mark 200 to be shown on the monitor 50 at the position corresponding to the position to which the fixation target has been moved. In this case, the fixation-target image 36' can be electrically formed (displayed) on the monitor 50 based on the detected position to which the fixation target has been moved.

Figure 6:
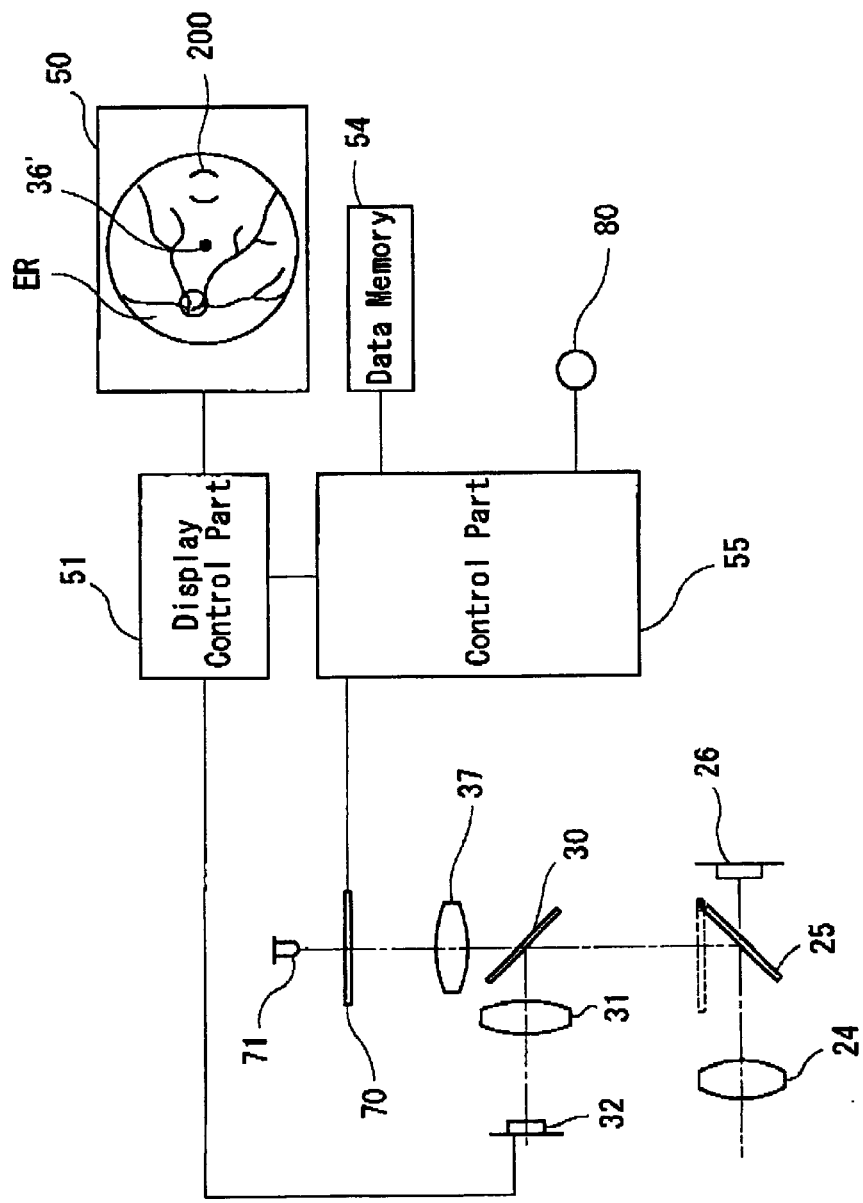
FIG. 6 is a view showing another method of presenting the fixation target which can be moved to a desired position.

Further, a liquid crystal display (LCD) may be also used to present a fixation target capable of moving to a desired position, and this case is illustrated in FIG. 6. An LCD 70 is placed at a position conjugate with the fundus Ef and the imaging surface of the camera 32, and a light source 71 is disposed behind the LCD 70. A light-transmitting portion is formed partially in a light-shielding portion of the LCD 70. The control part 55 controls a position of the light-transmitting portion, and the light-transmitting portion illuminated by the light source 71 is determined as the point light source 36. Then, the examiner operates a fixation-target moving switch 80 such as a cross key, thereby moving the light-transmitting portion to a desired position. In this case, the fixation-target image 36' can be electrically formed (displayed) on the monitor 50. In addition, it may be also possible to store the position where the guide mark 200 set in the mark-setting mode is to be formed (displayed), as the position of the light-transmitting portion of the LCD 70.

As described above, the present invention facilitates placing a position for displaying a fixation target at an intended position. Accordingly, in the case of photographing the same part of a fundus, reproducibility is enhanced, and an on-target photographed image can be obtained. Further, since plural guide marks can be displayed at different positions, thereby facilitating photographing different parts of the fundus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:
   an observation optical system having an objective lens and a photographic element for photographing a fundus of an eye to be examined via the objective lens, the fundus being illuminated by illumination light for observation;
   a monitor on which an image of the photographed fundus is displayed;
   a fixation-target presenting optical system for presenting a fixation target via the objective lens so that the fixation target is visually identified by the eye;
   a fixation-target moving unit by which a position for presenting the fixation target is moved to a desired position;
   a first display control unit by which the position of the fixation target to be moved is superposed on the fundus image to be displayed on the monitor; and
   a second display control unit by which a guide index for moving the fixation target is displayed at a desired position on the monitor.

2. The fundus camera according to claim 1, wherein the second display control unit graphically displays the guide index at plural positions on the monitor.

3. The fundus camera according to claim 1, wherein the second display control unit includes position setting means for setting the position for displaying the guide index on the monitor, a memory for storing data about the set display position, and display control means for displaying the guide index on the monitor based on the stored display position data.

4. The fundus camera according to claim 3, wherein the position setting means is capable of setting the plural positions for displaying the guide index, and wherein the display control means graphically displays the guide index.

5. The fundus camera according to claim 3, wherein the position setting means is capable of setting the plural positions for displaying the guide index, and wherein the memory is capable of storing plural placement patterns having different positions for displaying the guide index.

6. The fundus camera according to claim 5, further comprising selecting means for selecting any one of the stored placement patterns, and wherein the display control means reads the selected placement pattern from the memory and displays the guide index based on the read placement pattern.

7. The fundus camera according to claim 3, further comprising right-and-left eye designating means for designating one of right and left eyes to be examined, and wherein the memory is capable of storing information about designating the right or left eye to be examined by associating it with the set display position data.

8. The fundus camera according to claim 7, wherein the display control means displays the guide index on the monitor based on the display position data having been associated with an eye having been stored when an eye not having been stored is designated.

9. The fundus camera according to claim 1, wherein the fixation-target presenting optical system includes a point light source, and wherein the fixation-target moving unit includes a light-source moving unit by which the point light source is moved.

10. The fundus camera according to claim 1, the fixation-target presenting optical system includes a liquid crystal display having a light source at the rear thereof, and wherein the fixation-target moving unit includes an image control unit by which a position of a light-transmitting portion of the liquid crystal display is moved.

* * * * *